United States Patent [19]

Hillman et al.

[11] Patent Number: 5,088,978
[45] Date of Patent: Feb. 18, 1992

[54] APPARATUS AND METHOD FOR IONTOPHORETIC TRANSFER

[75] Inventors: Robert S. Hillman; John M. Pawelchak, both of San Diego, Calif.

[73] Assignee: Gensia Pharmaceuticals, Inc., San Diego, Calif.

[21] Appl. No.: 471,296

[22] Filed: Jan. 26, 1990

[51] Int. Cl.⁵ ............................................. A61N 1/30
[52] U.S. Cl. ................................................ 604/20
[58] Field of Search ................ 604/20; 128/639, 802, 128/803

[56] References Cited

U.S. PATENT DOCUMENTS

| | | | |
|---|---|---|---|
| 3,027,333 | 3/1962 | Friedman | 128/639 |
| 3,567,657 | 3/1971 | Lichtenstein | 128/639 |
| 3,989,050 | 11/1976 | Buchalter | 128/803 |
| 4,362,165 | 12/1982 | Carmon et al. | 128/803 |
| 4,406,827 | 9/1983 | Carim | 128/639 |
| 4,702,732 | 10/1987 | Powers et al. | 128/803 |
| 4,842,577 | 6/1989 | Konno et al. | 128/803 |
| 4,927,408 | 5/1990 | Haak et al. | 604/20 |

FOREIGN PATENT DOCUMENTS

| | | | |
|---|---|---|---|
| 0058920 | 9/1982 | European Pat. Off. | 604/20 |
| 2184016 | 6/1987 | United Kingdom | 604/20 |

Primary Examiner—C. Fred Rosenbaum
Assistant Examiner—Sharon Rose
Attorney, Agent, or Firm—Lyon & Lyon

[57] ABSTRACT

An apparatus and method for iontophoretic transdermal delivery of exercise simulating agents includes an electrode having disposed therein a drug reservoir comprising a viscosity-control agent comprising an aqueous sol with an antioxidant, a preservative, a chelator and a buffer. A silver/silver chloride conducive element is preferably situated in the electrode adjacent the drug reservoir to conduct an electric charge across the reservoir.

10 Claims, 4 Drawing Sheets

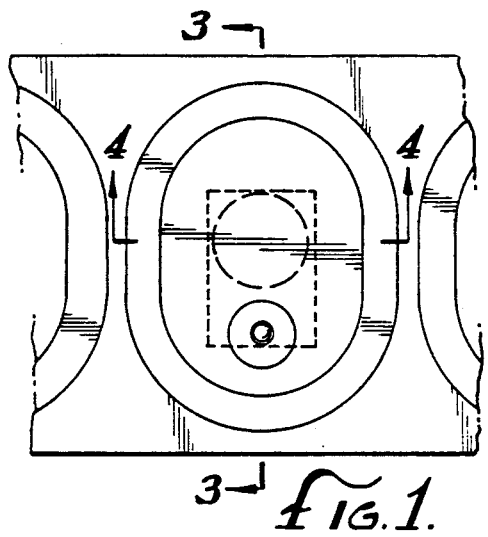
fig.1.
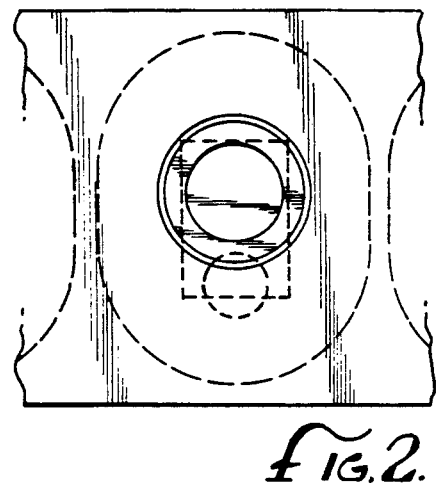
fig.2.
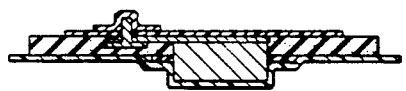
fig.3.
fig.4.
fig.5.
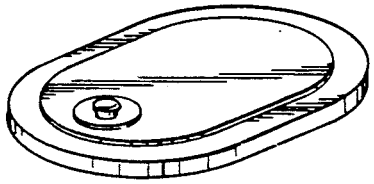

APPARATUS AND METHOD FOR IONTOPHORETIC TRANSFER

FIELD OF THE INVENTION

The present invention relates generally to a system for transdermal drug delivery, and more particularly, a system for iontophoretic delivery of exercise simulating agents for the diagnosis, evaluation and treatment of coronary artery disease.

Iontophoresis is the transport of ionized or charged species by application of an electrical current. Transdermal iontophoresis is the transport of an ionic drug through a patient's skin by application of a current through a drug containing electrode placed against the skin. A second electrode, termed the return or indifferent electrode, is also placed against the skin, normally several inches from the first. The current is evoked by applying a potential between the electrodes in either a constant DC, a pulsed DC or AC mode. It carries the ionized drug "through" the stratum corneum into the dermis where the drug diffuses into the capillaries situated near the dermal-epidermal junction, and into the systemic circulation.

Exercise simulating agents are drugs that elicit acute and adaptive cardiovascular responses similar to the types of responses elicited by aerobic activity. They are particularly useful, therefore, as a substitute for exercise stress testing for diagnosing cardiovascular diseases, due to their ability to increase heart rate, myocardial contractility, arterial blood pressure, and coronary and skeletal muscle blood flow. Exercise simulating agents that are ionic and of sufficient potency can be advantageously delivered using iontophoresis.

Flux refers to the amount of drug transported across the skin into the circulation per area per unit time. Flux is proportional to the applied electrical potential and the drug concentration. To achieve clinically effective transdermal iontophoretic delivery, the drug flux must be sufficiently large under the application of DC currents that do not damage the skin. Generally, the upper limit of current density is taken to be 0.5 mA/cm2. Other limits on flux include drug solubility, the partition coefficient of drug in the stratum corneum, and the drug's iontophoretic mobility.

Iontophoretic mobility requires that the drug be ionized or in charged form at some specific pH. Reduced iontophoretic efficiency can result from the presence of other ionic species in the formulation. These additional ions will "compete" with the drug in carrying current and can drastically reduce iontophoretic flux. Additional problems in iontophoretic delivery include electrical burns, dermal irritation, incompatibility between the drug and other excipients in the drug-containing medium, slow onset of pharmacologic activity and lack of drug delivery response to application and removal of current, drug degradation due to anodic current flow, pH change, and unsatisfactory drug storage capability. These problems must be overcome if safe, reliable and convenient medical iontophoresis is to be achieved.

A number of iontophoretic (and noniontophoretic) electrode and delivery systems have been proposed. See e.g., U.S. Pat. Nos. 3,977,392; 4,557,723; 4,640,689; 4,383,529; 4,474,570; and 4,722,726 and EPO Patent Nos. 182,520 and 252,732.

Three types of electrodes have been specifically proposed for iontophoresis, these being classified as: (1) monolithic pad; (2) reservoir pad; and (3) multilayer pad. A monolithic electrode pad design provides for including the drug in a polymer that is attached to the electrode. The polymer may contain an adhesive to maintain contact with the patient's skin. The drug is dispersed in the polymer during manufacture; this material is then formed into the pad itself. An example of the class of polymers suitable for use in such pads are hydrogels such as poly(hydroxy ethyl methacrylate) (HEMA).

A reservoir electrode pad design allows for addition of the drug to an electrode which comprises a disk which is attached to the patient's skin. In such a design, the drug is contained in a reservoir or cavity in the electrode itself. The reservoir or cavity is formed during the manufacture of the electrode. The drug can be added in gel form during manufacture of the pad, after its manufacture, or immediately prior to use.

A multilayer electrode pad includes separate layers for a buffering solution, an ion-exchange membrane and a drug reservoir.

The present invention provides a transdermal iontophoretic drug delivery system which includes an electrode and a drug gel formulation capable of delivering pharmacologically effective quantities of drug within the limits of acceptable current density without drug incompatibility with the other formulation excipients, which allows for appropriate onset times, which exhibits absence of drug degradation, and which should be well tolerated by the patient.

SUMMARY OF THE INVENTION

The present invention is directed to a novel transdermal iontophoresis transport system having optimal flux capability, rapid flux response to application and removal of current, minimal drug degradation due to anodic current flow, minimal pH change and satisfactory drug storage capability. To that end, a novel drug reservoir is provided in combination with a conductive member of unique design in a compact adhesive electrode. An indifferent electrode is employed therewith and both electrodes are adapted for use with an external power and control source.

BRIEF DESCRIPTION OF THE DRAWINGS

FIG. 1 is a top view of an electrode constructed in accordance with the present invention.

FIG. 2 is a bottom view of an electrode constructed in accordance with the present invention.

FIG. 3 is a cross-sectional view taken along line 3—3 in FIG. 1 of the electrode shown in FIGS. 1 and 2.

FIG. 4 is a cross-sectional view taken along line 4—4 in FIG. 1 of the electrode shown in FIGS. 1 and 2.

FIG. 5 is a perspective view of the electrode shown in FIGS. 1 to 4.

DETAILED DESCRIPTION OF THE PREFERRED EMBODIMENT

Figure 6:
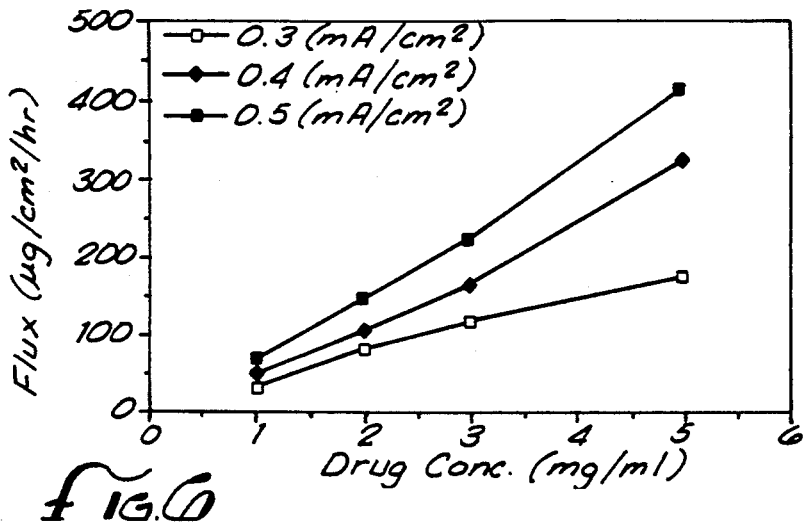
FIG. 6 is a graph showing flux as a function of drug concentration at various current densities.

The drug delivery system of the present invention is adapted for transdermal iontophoretic delivery of exercise simulating agents, such as analogs of amino isopropanol (metoprolol, propranolol) and catecholamines (Dobutamine, salbutamol, KM-13, isoproterenol). Certain preferred exercise simulating agents and their synthesis are disclosed in the commonly-assigned copending U.S. patent application, Ser. No. 308,683 for "Diagnosis, Evaluation and Treatment of Coronary Artery Disease by Exercise Simulation using closed Loop Drug Delivery of an Exercise Simulating Agent Beta Agonist," filed Feb. 9, 1989, the disclosure of which is incorporated by reference herein. Of particular interest is a novel exercise simulating agent beta agonist identified as GP-2-121-3. 1-(3,4-dihydroxyphenyl)-2-(4-(4-hydroxyphenyl)butylamino)ethanol hydrochloride, the R-enantiomer ("GP-2-121-3") and racemic mixture ("GP-2-124-3") are disclosed in the above-noted commonly-assigned and copending application Ser. No. 308,683, the contents of which are incorporated herein by this reference. These compounds possess a secondary amino moiety which is largely protonated below approximately pH 7 to provide an ionic species capable of iontophoretic response.

As used herein, GP 2-121-3 refers to the R-enantiomer of 1-(3,4-dihydroxyphenyl)-2-(4-(4-hydroxyphenyl)-butylamino)ethanol hydrochloride and GP 2-124-3 refers to the racemic mixture (mixture of R- and S- enantiomers of 1-(3,4-dihydroxyphenyl)-2-(4-(4-hydroxyphenyl)-butylamino)ethanol hydrochloride.

The system comprises generally a drug electrode having disposed therein a gel-like formulation containing a viscosity-control agent dispersed to form an aqueous sol with excipients such as an antioxidant, preservative, chelator and buffer to maintain a pH (4–5) at which the drug is dissolved in its protonated form. This formulation yields superior flux rates and rapidity of onset and offset of drug delivery when current is applied or removed. The system further includes an indifferent electrode containing the viscosity-control agent, preservative, electrolyte and a buffer at pH 4-7. Pharmaceutically, both formulations are physically and chemically stable upon storage, resistant to changes in pH and non-supportive of microbial growth. In addition, the formulas allow manufacture and filling by practical techniques.

I. THE ELECTRODE AND ITS FORMULATION

As shown in the Figures, the drug containing electrode is generally ovular, although many other shapes could be advantageously employed, provided the electrode is conformable to the area of the body where it is to be applied. The electrode includes interiorly disposed drug delivery components and an exterior support framework.

The drug delivery components include a gel reservoir or pad sandwiched between a conductive strip and an exterior mesh element. The gel reservoir, conductive strip and mesh elements are laterally coextensive. The cross-sectional area of the reservoir may be up to about 10 cm$^2$, but preferably is only as large as required to keep current density below 0.5 mA/cm$^2$, since increased pad area reduces current density, which may be a major factor in pH change, damage to the patient's skin and build up of a drug depot. The preferred reservoir contains about 1 ml volume and has an area of 1.8 cm$^2$. The depth is in a range of 3–10 mm and is preferably about 5 mm.

The conductive strip is preferably formed of a silver impregnated mylar strip chloride by an electrode discharge process. As thus formed, the electrode undergoes an oxidation reduction reaction during iontophoretic delivery whereby silver chloride is produced from chloride ions in the drug itself, which is a hydrochloride amine salt. This provides a highly uniform silver-silver chloride contact boundary that enhances flux and minimizes skin irritation by counteracting the formation of highly mobile ions such as H+, which not only compete with the ionized drug for available current, but also decrease pH.

The mesh element helps retain the drug in the gel reservoir during storage. Before the electrode is attached to the patient, the mesh element must be removed.

The drug delivery reservoir is encased in a circumferentially arranged support frame comprising a continuous adhesive foam member. The support frame is shown to be generally rectangular in cross-section although other shapes could be employed. Preferably, the support frame is slightly thinner than the drug delivery components so that when the conductive strip is flush with one side of the frame, the reservoir element extends slightly beyond the other side of the frame to ensure contact of the gel reservoir mesh with the patient's skin. Moreover, it is preferred that the drug delivery elements be slightly larger than the interior of the support frame so as to be retained therein by compressive engagement.

As shown in the figures, an insulative vinyl backing member may be secured to the top of the support frame. Mounted to and extending through the backing member is a conductive snap connector. The snap is electrically attached to a tongue extending from the conductive strip and is adapted for connection to an external power and control source (not shown).

Current from the power and control source enters the electrode through the snap, at a location laterally disposed from the drug reservoir. The current flows uniformly through the reservoir by means of the conductive strip, which is coextensive therewith, and thereafter through the patient to the second, indifferent electrode (not shown). The indifferent electrode is constructed in accordance with the drug delivery electrode herein described, except that no drug reservoir need be provided. For ease of identification, the drug and indifferent electrodes may be color coded.

For storage purposes, a release liner may be removably attached to the bottom of the support frame to help retain the gel during storage and shipping.

The preferred viscosity control agent employed in the gel reservoir formulation is hydroxypropylmethyl cellulose, particularly suitable is that which is sold commercially under the trademark METHOCEL® (hydroxypropyl methylcellulose). Of the METHOCEL® (hydroxypropyl methylcellulose) grades available, E10M was determined to be preferable. METHOCEL® (hydroxypropyl methylcellulose) E10M is generally compatible with the catecholamine and amino isopropanol exercise simulating agents of interest, non-irritating, able to restrict flow for convenient processing, water dispersible, non-ionic, of standard, compendial grade, commercially available, and a poor substrate for microbial growth. Other viscosity control agents known to those skilled in the art of which have the above noted qualities of METHOCEL ® (hydroxypropyl methylcellulose) may be substituted.

The METHOCEL ® (hydroxypropyl methylcellulose) E10M content employed may be between 4% and 10% (w/v) and is preferably 4% (w/v). This yields a matrix that resists flow sufficiently to remain in the electrode reservoir in any orientation during filling, processing and when covered with a mesh element during prolonged storage in an on-side or inverted position. At the same time, reasonably low yield and viscosity are provided to allow for easy mixing, filling and bubble elimination. METHOCEL ® (hydroxypropyl methylcellulose) E10M further allows adequate transport to support anodic oxidation, which is necessary to facilitate an effective anodic reduction oxidation reaction.

The preferred antioxidant employed in the reservoir formulation is sodium metabisulfite between 0.1–10% (w/v) and preferably 0.1% (w/v). At this relatively low concentration, the possibility of sulfonate formation and sensitization is minimized. Moreover, the possibility of bisulfite transport across the skin is also negligible due to the fact that any transdermal migration would be opposed by the charge on the drug electrode, which would attract the bisulfite ions. Even assuming electrode polarity is reversed, significant bisulfite transport would not occur because the fraction of the current carried by bisulfite is low in comparison to chloride which is present at a higher concentration and is more mobile.

The disodium salt of EDTA is incorporated as a chelator to prevent metal catalyzed autoxidation of the drug. It is effective at low concentrations (e.g. between 0.001–0.05% w/v, preferably 0.01% w/v), water soluble, compendial, used in parenteral dosage forms and exhibits satisfactory binding constants at pH 4–5. Because of its low binding constant, EDTA does not interact significantly with silver at this concentration and pH. The low concentration does not appreciably affect iontophoretic function.

A buffer at pH 4–5 is incorporated in the drug electrode (anode) formula to resist pH changes associated with proton generation from water, to decrease the drug's oxidation potential and tendency to racemize or form sulfonates and to ensure the effectiveness of the antioxidant by regulating the bisulfite/sulfite ionic equilibrium. The system employed is 0.005–0.05M, preferably 0.01M citric acid/citrate. This amount of citrate contributes significantly to the ionic strength at low drug concentrations.

The reservoir formulation also includes a preservative, preferably comprising a mixture of parabens (0.10–0.20% w/v, preferably 0.18% w/v methyl and 0.02–0.04% w/v, preferably 0.02% w/v propyl). This mixture is soluble, effective at low concentrations and non-ionic.

In a preferred embodiment, the drug electrode reservoir is manufactured as follows:

1. The citric acid, EDTA and bisulfite are dissolved in about one-half the final volume of water, and the pH is adjusted to 4–5. The drug is added and dissolved.
2. The parabens are dissolved in about one-half of the volume at boiling.
3. The total amount of E10M is dispersed in the parabens solution.
4. The hot dispersion is cooled to 40°–50° C.
5. The drug solution is added mixing thoroughly.
6. Bubbles are removed by centrifugation and the formula is filled into the anodic electrode reservoir.

The indifferent electrode reservoir is of similar formulation and comprises 4–10%, preferably 4% E10M, 0.1–0.5%, preferably 0.28% NaCl, 0.1–0.5%, preferably 0.2% parabens, 0.10–0.20%, preferably 0.12% $NaH_2PO_4$, and 0.1–0.2%, preferably 95.4% water. This electrode reservoir is manufactured as follows:

1. The parabens are dissolved in about one-half the required volume of water at boiling. The E10M is added and dispersed.
2. The other ingredients are dissolved in the other half.
3. The fluids are combined when the E10M dispersion has cooled to 40°–50° C., and mixed well.
4. Bubbles are removed by centrifugation and the formula is filled into the cathodic electrode reservoir.

II. IONTOPHORETIC FUNCTION AND CHEMICAL STABILITY OF THE ELECTRODE RESERVOIR FORMULATION

The iontophoretic response and stability of the drug reservoir formulation were employed as a means of formula screening. Several criteria for acceptability were used:

A drug flux of 100 micrograms per $cm^2$ per hour, at a current density of not more than 0.5 $mA/cm^2$, was considered necessary for adequate pharmacodynamic response.

A response of flux with current density varying from 0.2 to 0.5 $mA/cm^2$ was desired. Such a relationship is, ideally, linear.

A pH change of not more than 1.0 units could be tolerated.

Significant drug degradation due to anodic current flow was to be avoided.

Rapid response to the application and removal of current was desired.

Reproductibility of iontophoretic response and drug stability upon aging (storage) was required.

A. Evaluation Of Iontophoretic Function Of Formulation Comprising Isoproterenol Iontophoretic flux of an E10M METHOCEL ® (hydroxypropyl methylcellulose) formulation containing Isoproterenol as a function of drug concentration at various current densities is shown in FIG. 6. As indicated, the required ug/cm2/hr flux is readily achieved. The flux response is also linear.

B. Evaluation Of Iontophoretic Function Of Formulation Comprising GP-2-124-3

The racemic modification GP-2-124-3 was used to determine the response of an electrode containing GP-2-121-3. In solution they are iontophoretically equivalent and experimentally based conclusions using GP-2-124-3 are believed to be directly applicable to GP-2-121-3.

Figure 7:
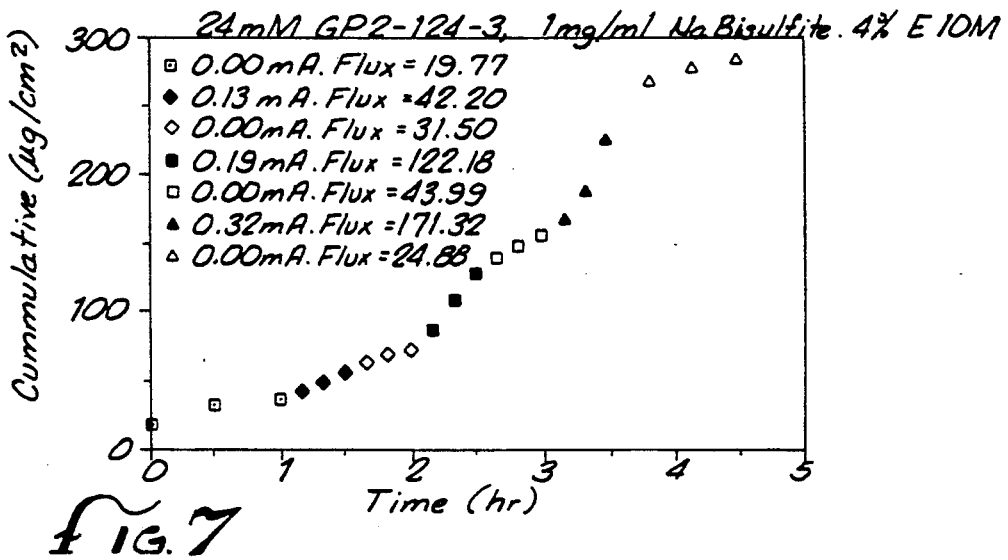
FIG. 7 is a graph showing cumulative flux as a function of time at various currents.

Results from a typical study using GP-2-124-3 at 24 mM (8.5 mg/ml) in 4% E 10M with 0.1% sodium metabisulfite are shown in FIG. 7. The fluxes obtained at current densities of 0.2, 0.3 and 0.5 mA/cm² are 42, 122 and 172 mcg per cm² per hour respectively. The flux is well above the estimated anticipated requirement of 100 mcg per cm² per hour at 0.5 mA/cm² established as a lower limit.

It is also clear from the results of this experiment that formulations composed of drug with E10M and antioxidant exhibit another required characteristic. Significant flux occurs only during current application; essentially negligible flux occurs once the current is switched off. This supports the adequacy of the onset/offset time with current.

Figure 8:
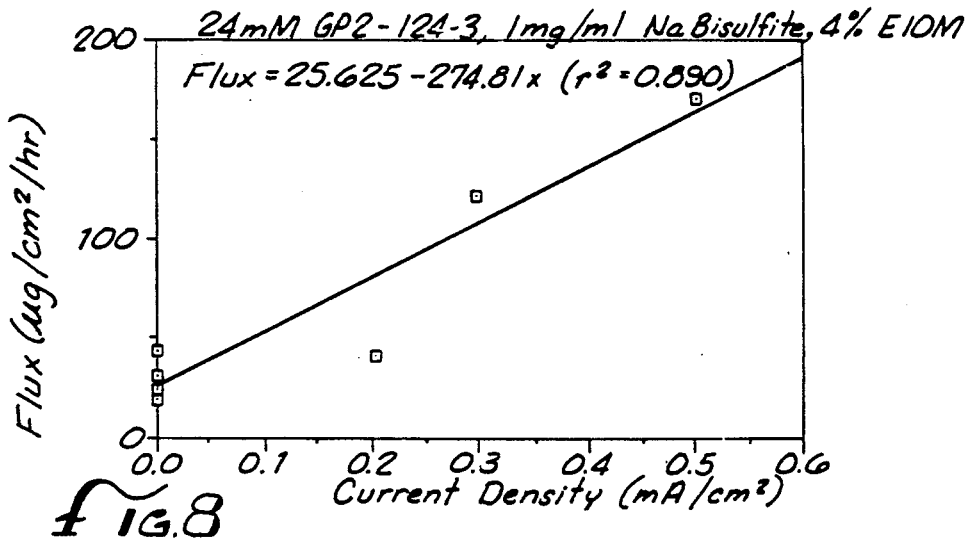
FIG. 8 is a graph showing flux as function of current density based upon a least squares fit of the data presented in FIG. 7.

FIG. 8 illustrates the agreement of current and flux, another formulation goal, based on the least squares fit of the data from FIG. 7.

C. Absence Of Drug Degradation Due To Current Application

To confirm that the drug does not degrade with the application of current, a DC current of 0.7 mA was applied for 45 minutes across two electrodes containing 50mM GP-2-124-3 and joined at the formulation reservoir faces. No significant drug degradation was detected from an examination of HPLC chromatograms of treated formulations. This result indicates the drug is not appreciably degraded when subjected to exaggerated current application in the anodic electrode.

D. Iontophoretic Response And Chemical Stability Of Aged Gel Formulations

1. A series of electrodes filled with 70 mM GP-2-124-3 gel with 4% gel with 4% E10M, 0.1% metabisulfite, 0.01% Na₂EDTA, 0.18% methyl paraben, 0.02% propyl paraben and 0.01M citrate (pH4.5) was examined for iontophoretic response and chemical stability during storage at room temperature (25° C.) of RT and 4° C. for up to eleven weeks. This study was undertaken to evaluate the effect of aging on the reproducibility of flux and to evaluate chemical stability.

Figure 9:
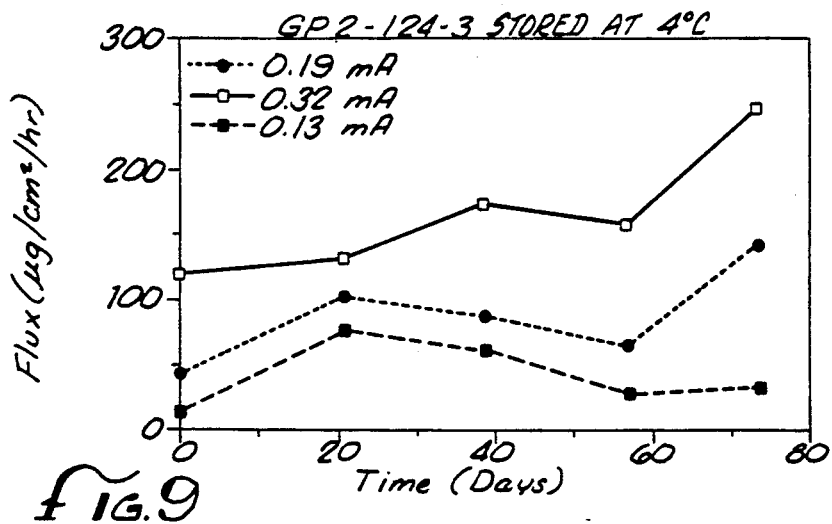
FIG. 9 is a graph showing flux as a function of time at various currents wherein the drug is GP 2-124-3 stored at 4° C.
Figure 10:
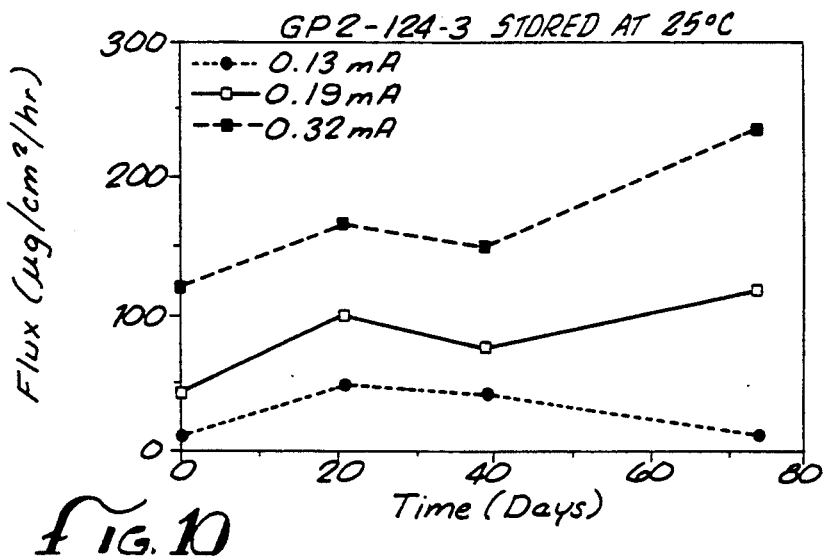
FIG. 10 is a graph showing flux as a function of time at various currents wherein the drug is GP 2-124-3 stored at 25° C.

No significant degradation was observed using an isocratic HPLC assay. Although there was considerable variation in the flux values measured at zero, three, six and eleven weeks, due to skin variation no definite trends emerged. The flux values for the formula stored at both temperatures are similar. Plots of the flux values at each storage temperature as a function of time at the current densities employed are shown in FIGS. 9 and 10.

2. Gel formulations containing 24 mM GP-2-121-3 with 4% E10M, 0.1% NaBisulfite, 0.18% Methyl paraben and 0.02% propyl paraben were stored at 4° C. The iontophoretic response was measured at zero, 8, 21 and 44 days. No chemical assays were performed.

Figure 11:
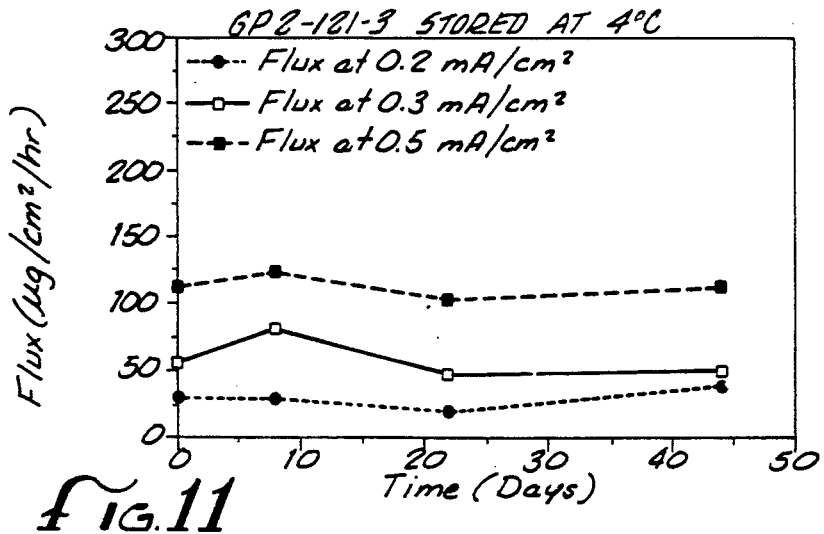
FIG. 11 is a graph showing flux at various current densities as a function of time wherein the drug is GP 2-121-3 stored at 4° C.

The flux data as a function of current density, after aging, are presented in FIG. 11. This study indicates relatively minor changes in iontophoretic response accompany low-temperature storage of E10M formulations of GP-2-121-3. The data again reveals that rather large variations are inherent in the results of flux experiments. Because no trends can be defined, no specific changes can be ascribed to storage.

E. Relationship Of Drug Flux To Current And Concentration

Figure 12:
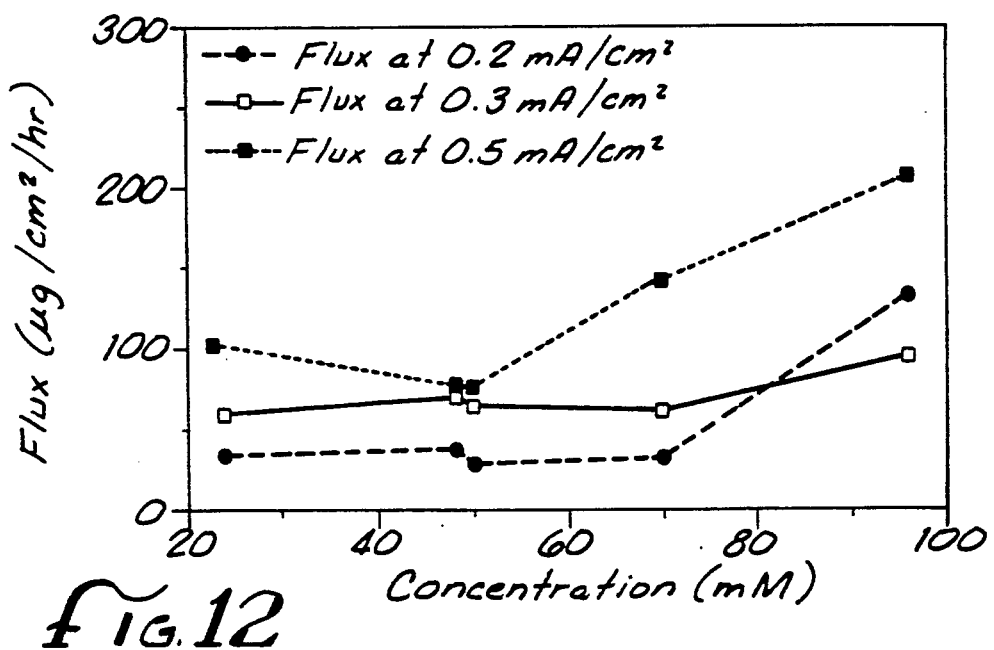
FIG. 12 is a graph showing flux as a function of drug concentration at various current densities.

Iontophoretic transport studies were carried out for similar formulations of GP-2-121-3 and the racemic form GP-2-124-3 at concentrations from 24 to 96 mM. Results from these studies are presented in FIG. 12.

Based on mean values, the results indicate an increase in flux with current and concentration. The iontophoretic response of enantiometric and racemic drug is felt to be equivalent. These data are compared allowing for the variability of the epidermis used and the inter-experiment variations in technique and assay. Changes in pH were within the desired 1.0 unit limit.

The range of iontophoretic fluxes indicates that GP-2-21-3 may be delivered at rates anticipated to elicit pharmacodynamic responses at current densities between 0.2 and 0.5 mA/cm² using drug concentrations from 24 to 96 mM. Iontophoretic response is believed more sensitive to current at higher currents due to competition by added electrolytes such as buffer which carry a larger portion of the current at low drug loads.

III. PREPARATION OF GP 2-121-3

Preparation of 1-(3,4 dihydroxyphenyl)-2-(4-(4-hydroxyphenyl)-butylamino)ethanol hydrochloride

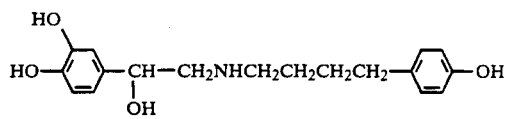

The R-enantiomer is prepared by the procedures described below; some S-enantiomer may be prepared also.

(a) Preparation of 4-(4-Hydroxyphenyl)butanol

To a solution of 4-(4-methoxyphenyl)butanol (100 g, 0.55 mole) in dichloromethane, cooled to −75° C. in a dry ice-acetone bath, a solution of boron tribromide (278 g; 2.0 mole) was added slowly over one hour. The cooling bath was then removed and the reaction mixture allowed to warm to 15° C. slowly. The reaction was shown to be complete by thin layer chromatography (TLC). The reaction mixture was again cooled in an ice-water bath; 10% sodium hydroxide solution was added until pH of about 9 was obtained. The resulting mixture was then acidified with concentrated HCl to a pH of about 2. The organic layer was separated, the aqueous layer was extracted once with ethyl acetate. The combined organic layers were dried over magnesium sulfate, filtered and concentrated to give 90 g of crude product. The crude product was purified by dry filtration chromatography using 10% ethyl acetate/dichloromethane as eluent giving an 86% yield of pure 4-(4-hydroxyphenyl)butanol. The ¹H NMR was consistent with the assigned structure.

(b) Preparation of 4-(4-Benzyloxyphenyl)butanol

To a solution of 4-(4-hydroxyphenyl)butanol (125 g, 0.75 mole) in acetone 0.85.8 g (1.25 mole) anhydrous potassium carbonate (285.8 g, 1.25 mole) was added, followed by 160.8 (0.94 mole) benzyl bromide. The reaction mixture was then heated at reflux for 25 hours. After cooling to room temperature, the reaction mixture was filtered and the filter cake washed with acetone. The filtrate was concentrated to dryness. The solid residue was washed twice with 500 ml hexane. After drying under high vacuum overnight, 161 g of the desired product were obtained, which was homogeneous on TLC. The ¹H NMR spectrum was consistent with the assigned structure.

(c) Preparation of 4-(4-Benzyloxyloxyphenyl)butanal

To a solution of 4-(4-benzyloxyphenyl)butanol (170.0 g, 0.66 mole) in dichloromethane cooled in an ice-water bath, 215.0 (1.0 mole) pyridinium chlorochromate was added in portions. After the addition was complete, the cooling bath was removed. The reaction mixture was stirred vigorously while warming to room temperature. After 3 hours, the dark brown solution was decanted; 1.5L of ether was added to the residue. The residue was stirred in ether for 15-30 minutes and then filtered. The organic extracts were combined and filtered through a bed of bentonite. The clear filtrate was dried over magnesium sulfate, filtered and concentrated to afford a near quantitative yield of crude aldehyde (166 g). Purification of the crude aldehyde by dry filtration chromatography using 3% hexane/ethyl acetate as eluent gave 134 g of product. The $^1$H NMR spectrum was consistent with the assigned structure.

(d) Preparation of 1-(3,4-Dihydroxyphenyl)-2-(4-(4-hydroxyphenyl)-butylamino)ethanol hydrochloride To a 3.8L pressure vessel, was charged methanol containing 2% acetic acid (2.6L) and (R)-norepinephrine (44.0 g, 0.26 mole) followed by $PtO_2$ (5.86 g) and Pd/C (3.9(g). The mixture was then hydrogenated under 15 psi for 15 minutes. The above butanal (85.9 g 0.34 mole) was added to the mixture and hydrogenation continued at 30 psi for 24-48 hours. The catalysts were removed by filtration. The filtrate was concentrated under reduced pressure to dryness. The crude product was purified by filtration chromatography using dichloromethane/methanol/acetic acid (10:2:0.1) as eluent. The fractions containing the desired product (Rf=0.45, dichloromethane/methanol/acetic acid, 8:2:1) were pooled and concentrated to dryness. The residue (18.0 g) was dissolved in methanol, treated with Dowex 50 X-8 resin and filtered. The filtrate was acidified with concentrated HCl to a pH of about 4, concentrated to a small volume, and then added to anhydrous ether. The desired hydrochloride salt precipitated from the solution, was collected and dried under high vacuum to give 13.5 g of product. Further purification of the fractions containing a mixture of products and Dowex-5 8X treatment gave an additional 12.5 g of slightly less pure product. The first crop of salt was further purified by dissolving in water, filtering and lyophilizing; mp 55°-58° C.; $[\alpha]_D(23°$ C.)$=-18.5$ (C=1.0, $C_2H_5OH$); I.R. 3500, 1600, 1250 $Cm^{-1}$; $^1$H NMR (DMSO-$d_6$) δ 8.95 (d,2H,OH), 8.90-8.50 (brd s,2H,NH, OH), 7.00-6.60 (m, 7H, ArH), 6.95 (d,2H, CHOH), 4.75 (m,1H,CHOH), 3.00-2.90 [m,4H,$CH_2N$), 2.50-2.40 (m,2H,$ArCH_2$), 1.70-1.50 (m,4H,$CH_2CH_2$).

Accordingly, an apparatus and method for iontophoretic transfer has been disclosed. While what has been hereinbefore described represents preferred embodiments of the invention, it will be recognized that other variations are possible, and the invention is not to be limited except as set forth in the claims appended hereto.

We claim:

1. A transdermal iontophoretic drug delivery system for delivering an exercise simulating agent comprising:
   an electrode including
      a metallic conductive element, and a gel reservoir, the gel reservoir being disposed adjacent to the metallic conductive element, and
      a gel disposed in the gel reservoir including a catecholamine analog as an exercise stimulating agent, a viscosity-control agent comprising hydroxypropyl methylcellulose dispersed to form an aqueous sol with an antioxidant, a preservative, a chelator and a buffer.

2. The delivery system set forth in claim 1 wherein said viscosity control agent is METHOCEL ® (hydroxypropyl methylcellulose) E10M.

3. The delivery system set forth in claim 1 wherein said viscosity control agent is METHOCEL ® (hydroxypropyl methylcellulose) E10M, said antioxidant is sodium metabisulfite, said preservative is a mixture of methyl and propyl parabens, said chelator is disodium salt of EDTA, and said buffer is citric acid/citrate.

4. The delivery system set forth in claim 1 comprising 4–10% (w/v) hydroxypropyl methylcellulose, 0.1–10% (w/v) sodium metabisulfite, 0.001–0.05% (w/v) disodium salt of EDTA, 0.001–0.05M citric acid/citrate, 0.10–0.20% (w/v) parabens which comprises a mixture of methyl and 0.02–0.04% (w/v) propyl.

5. The transdermal iontophoretic drug delivery system of claim 1 wherein the metallic conductive element includes silver.

6. The transdermal iontophoretic drug delivery system of claim 5 wherein the metallic conductive element is silver/silver chloride.

7. A transdermal iontophoretic drug delivery system for delivering GP-2-121-3 comprising:
   an electrode including a metallic conductive element, and
   a reservoir adjacent to the metallic conductive element,
   a gel disposed in the reservoir including GP-2-121-3, a viscosity control agent comprising 4–10% (w/v) hydroxypropyl methylcellulose, 0.1–10% (w/v) sodium metabisulfite, 0.0001–0.05% (w/v) disodium salt of EDTA, 0.005–0.05M citric acid/citrate, 0.10–0.20% (w/v) parabens which comprises a mixture of methyl and 0.02–0.04% (w/v) propyl.

8. The delivery system set forth in claim 7 further including a silver/silver chloride conductive element disposed in adjacent engagement with said reservoir.

9. The delivery system set forth in claim 8 further including an indifferent electrode comprising a reservoir having disposed therein 4–10% (w/v) hydroxypropyl methylcellulose, 0.1–0.5% sodium chloride, 0.10–0.20% (w/v) parabens, 0.10–0.20% (w/v) Sodium $H_2PO_4$ and 80–95% (w/v) water.

10. A method for iontophoretically delivering a catecholamine amino isopropanol exercise simulating agent comprising applying to a patient's skin a first electrode comprising a reservoir containing a substance to be iontophoretically delivered, said reservoir further comprising a viscosity control agent comprising 4–10% (w/v) hydroxypropyl methylcellulose, 0.1–10% (w/v) sodium metabisulfite, 0.001–0.05% (w/v) disodium salt of EDTA, 0.005–0.05M citric acid/citrate, 0.10–0.20% (w/v) parabens which comprises a mixture of methyl and 0.02–0.04% (w/v) propyl, said method further comprising securing a second electrode to the patient a short distance from said first electrode, said second electrode comprising a gel reservoir having disposed therein 4–10% (w/v) hydroxypropyl methylcellulose, 0.1–0.5% sodium chloride, 0.10–0.20% (w/v) parabens, 0.10–0.20% (w/v) Sodium $H_2PO_4$ and 80–95% (w/v) water, and applying an electrical potential across said electrodes.

* * * * *